United States Patent [19]

Vitovec et al.

[11] Patent Number: 4,696,683

[45] Date of Patent: Sep. 29, 1987

[54] METHOD AND EQUIPMENT FOR SEPARATION OF SOLIDS FROM GASEOUS MIXTURES

[75] Inventors: Jaroslav Vitovec, Prague; Jan Cermák, Karlstejn; Jirí Smolík, Prague, all of Czechoslovakia

[73] Assignee: Ceskoslovenska akademie ved, Czechoslovakia

[21] Appl. No.: 833,958

[22] Filed: Feb. 27, 1986

[30] Foreign Application Priority Data

Jul. 16, 1985 [CS] Czechoslovakia .................... 5276-85

[51] Int. Cl.$^4$ ............................................. B01D 59/08
[52] U.S. Cl. ........................................... 55/82; 55/267; 55/315; 55/429; 55/434; 549/250; 260/704
[58] Field of Search ...................... 55/82, 267.315, 392, 55/434, 342, 338, 429; 549/250; 260/704

[56] References Cited

U.S. PATENT DOCUMENTS

| | | | |
|---|---|---|---|
| 2,446,181 | 8/1948 | Kraus | 55/82 |
| 2,455,314 | 11/1948 | Pietsch | 55/82 |
| 2,692,657 | 10/1954 | Barton | 55/82 |
| 4,080,182 | 3/1978 | Vitrovec et al. | 55/269 |
| 4,246,012 | 1/1981 | Khopkov | 55/269 |
| 4,252,545 | 2/1981 | Haferkorn | 55/82 |
| 4,528,006 | 7/1985 | Vitrovec et al. | 55/269 |

FOREIGN PATENT DOCUMENTS

| | | | |
|---|---|---|---|
| 298343 | 10/1928 | United Kingdom | 55/434 |
| 794450 | 5/1958 | United Kingdom | 55/269 |
| 2125311 | 3/1984 | United Kingdom | . |
| 272800 | 9/1970 | U.S.S.R. | 55/319 |
| 270484 | 3/1971 | U.S.S.R. | 55/434 |

*Primary Examiner*—Bernard Nozick
*Attorney, Agent, or Firm*—Leydig, Voit & Mayer

[57] ABSTRACT

The invention solves a method and an apparatus for the separation of solids from gaseous mixtures especially the separation of phthalic anhydride after its desublimation from mixtures with vapours of sublimable substances, steam, air or inert gases, which originate at sublimation refining or at catalytic production of phthalic anhydride by air oxidation of naphthalene or o-xylene.

The flakes of phthalic anhydride, which originated after the decrease of temperature in the desublimator space were agglomerated and compacted due to the increase of velocity of gaseous mixture in contracted cross-section of the separator. The formed agglomerates are separated from the gaseous mixture and collected in a receiver well. From the well the agglomerates are transported by a conveyor or they are continuously melted. The melt formed outlets through a siphon. The rest 1 to 5% of phthalic anhydride is separated from gaseous mixture in a filter from wire net and by gradual melting is introduced into the receiver well.

6 Claims, 1 Drawing Figure

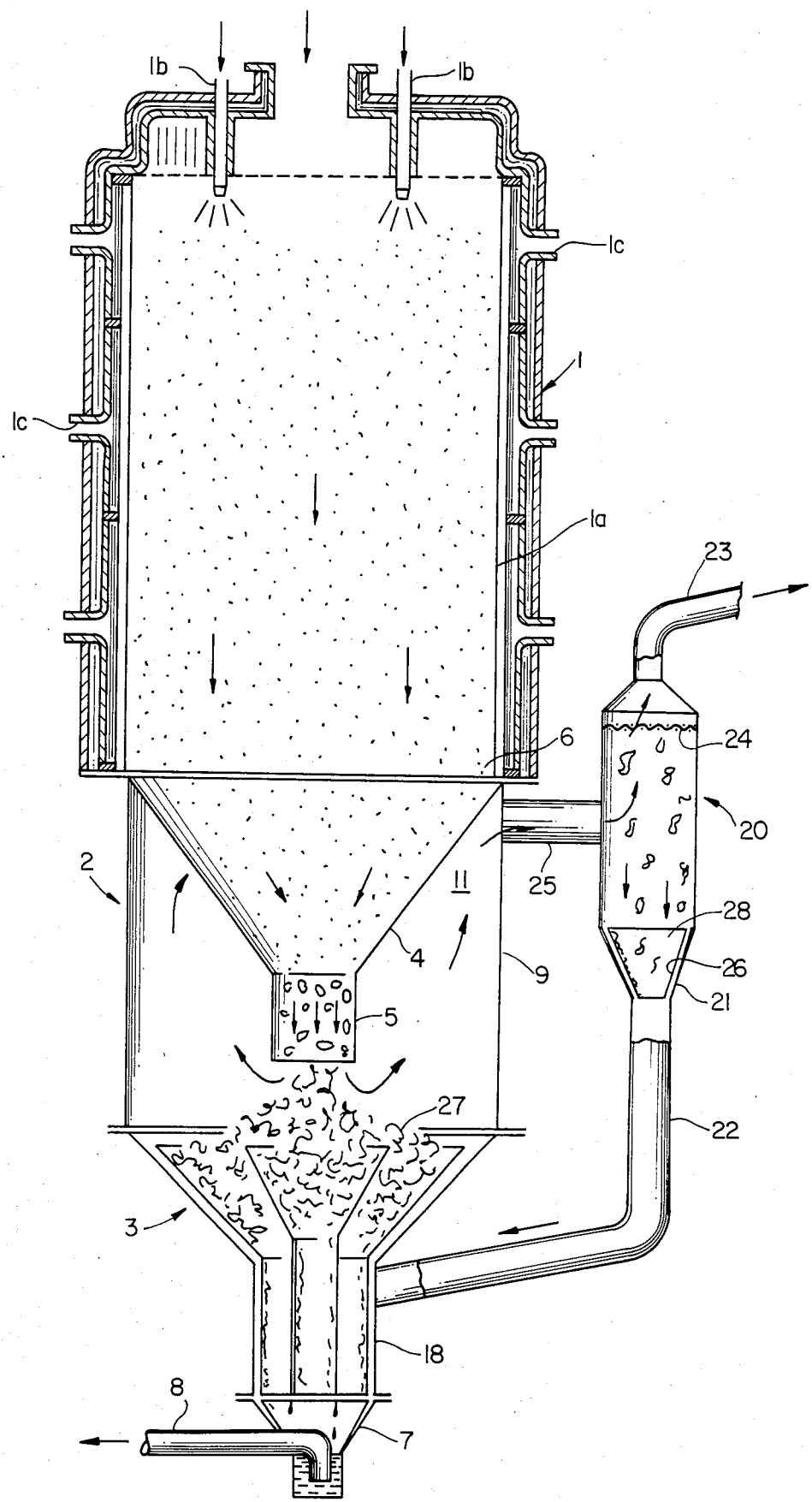

METHOD AND EQUIPMENT FOR SEPARATION OF SOLIDS FROM GASEOUS MIXTURES

BACKGROUND OF THE INVENTION

The invention describes a method and equipment for separation of solids from gaseous mixtures, especially for the separation of phthalic anhydride following its desublimation from a mixture with vapours of sublimable substances, steam, air or inert gases, which originate at sublimation refining or during production of phthalic anhydride by catalytic oxidation of naphthalene or o-xylene with air.

In Czechoslovak Pat. NO. 229768, corresponding to U.S. Pat. No. 4,528,006, a method is described together with an equipment for separation of phthalic anhydride from vapour-gaseous mixtures formed by oxidation of naphthalene or o-xylene with air. The mixtures are cooled from temperature in the region of 130° to 250° C. to the region of 50° to 100° C. by evaporation of water, which is sprayed into mixtures by nozzles in desublimation chamber. The openings of the nozzles are protected against the contact with the cooled vapour-gaseous mixture by washing with air, which is heated to the temperature of the input mixture.

This avoids the condensation of vapours and build up of solids on the nozzle openings. Simultaneously, air passes through gas permeable walls such as disclosed in U.S. Pat. No. 4,528,006, into a desublimator chamber. The temperature of the air is close to the temperature of the incomming gaseous mixture and it decreases later to a temperature which is lower than that of the mixture leaving the desublimator. Its velocity in the location of the entrance of the gaseous mixture is in the region of 10 to 1 cm/s depending upon the phthalic anhydride concentration in the mixture. It then gradually decreases to 1 to 0.2 cm/s. The velocity of vapour-gaseous mixture with desublimised solid products in the outlet from desublimizing space is in the region of 0.15 to 1 m/s.

The advantage of the method is the desublimation of bulks of mixtures without settling on the walls. Therefore, these walls need not be cleaned of a layer of solids. The several times higher throughput of the desublimation apparatus is a further advantage.

Vapour-gaseous mixtures which originate during the production of phthalic anhydride contain, however, tar like substances which at the separation of the product, stick to filter materials so that these filters must be periodically cleaned.

In addition to phthalic anhydride desublimizing in the form of wool flakes, which can hardly be transported from the apparatus, filtration equipment is complicated and explosion hazard is high at separation and transport.

These shortages are solved by a new continuous way of separation of solids especially of phthalic anhydride from vapour-gaseous mixture and by a new transport from the separator.

SUMMARY OF THE INVENTION

The basis of the patended method consists in acceleration of the flow of the mixture of the output from to a desublimator to a velocity in the region of 0.6 to 25 m/s and successively in the deceleration of it in the region of 0.15 to 1 m/s and simultaneous separation of 95 to 99% of solid phthalic anhydride from the mixture. It is an advantage to melt continuously the formed phthalic anhydride at gradually increasing temperatures of 120° to 180° C. The rest of the non separated phthalic anhydride can be then filtered off the mixture and the separated phthalic anhydride is continuously melted at gradually increasing temperatures of 120° to 180° C.

The apparatus for separation of solid substances from gaseous mixtures, especially for the separation of phthalic anhydride according to the above described method consists of a body of a separator in the upper part of which a vessel of conical shape is placed. The greater cross-section of it is formed as an entrance throat and the smaller cross-section is equipped as an output throat, which is the gate into a settling well. The well is located in the lower part of the body of the separator and an outlet device is connected with the well. The entrance neck of the separator can be directly connected to the outlet from a desublimator and the ratio of the cross-section of the outlet of the desublimator and of the cross-section of outlet neck of conical vessel is approximately 4 to 25. The outlet receiver of the separator can be equipped a heating device and in the upper part of the separator body it is advantageous to connect a filtration device, a filter made from wire net which is equipped with a outlet for the gaseous mixture, and an outlet which is connected with the receiver well of the separator.

The effects of the method consist in agglomeration and compacting phthalic anhydride flakes which is due to the increased velocity as well as in easy separation of the formed agglomerates of the flakes due to the consecutive decrease of velocity. In this way 95 to 99% of solid phthalic anhydride is separated, which can be consecutively melted so that in the entrance zone the temperature is kept in the region of 120° to 160° C. and that in the outlet zone it is from 140° to 180° C. This considerably simplifies the transport of phthalic anhydride from the desublimator, decreases transport and equipment costs and significantly reduces the explosion hazard at transport of the powdered phthalic anhydride. The rest of 1 to 5% phthalic anhydride which is carried away by gaseous mixture is filtered and, with the same advantages, continuously melted. At melting the rests of phthalic anhydride no phthalic anhydride is carried away into filter. Only long needle crystals are formed from its vapour stripped by gaseous mixture.

The apparatus for realizing the above mentioned method can be a part of a desublimator or it is made as a particular separator connected to the output of the desublimator. The increase of the velocity of the mixture is achieved by conical through flow vessel the contraction throat of which is the gate of a reception well, which is of the cross-section corresponding to the outlet from desublimator. This ensures the requested variations in velocity and with this connected separation of 99% of solid phthalic anhydride. With an advantage a wire net with openings 1 to 5 mm is used for additional filter, in which the majority is trapped of rests of the flakes of the stripped phthalic anhydride.

BRIEF DESCRIPTION OF THE DRAWINGS

The FIGURE is a cross section of the separator in relation to a desublimator.

In the following examples several actual realization of the invention are described including the apparatus which is shown in FIGURE enclosed. Example 5 illustrates the preferred embodiment as shown in the FIGURE. It is understood that the basic concept of the present invention is not limited to any particular type of embodiment. It is intended to cover all types of embodiments limited only to the true spirit and scope of the invention.

EXAMPLE 1

In a fluidized bed sublimator, phthalic anhydride was sublimized at the rate of 4 kg/h with 10 m$^3$ of air/h (20° C.) which corresponded to the velocity of the mixture of 0.15 m/s at 200° C. The formed vapour-gaseous mixture, having about 6% (vol) of phthalic anhydride in air was cooled in a desublimator (200 mm ID) by water spraying at 70° C. The gaseous mixture with flakes of solid phthalic anhydride went further through the vessel inside the desublimator which was conically contracted to I.D. 100 mm and, after a pass through the tube of the same I.D. and of the length 400 mm, when into the lower part of the desublimator of the original I.D. 200 mm. In the connected reception well 3.4 kg of solid phthalic anhydride per hour was separated, In the additional filter, from wire net with opening 5 mm, 0.55 kg of phthalic anhydride per hour was trapped. Sum of isolated phthalic anhydride equalled 3.95 kg per hour, which amounts to 98.8%.

EXAMPLE 2

Vapour-gaseous mixture of the composition of 1% phthalic anhydride in air (66 g/m$^3$) at 170° C. in a volume amount of 30 m$^3$/h (20° C.), which corresponds to the velocity of the mixture flow of 0.43 m$^3$/s (170° C.), was cooled in a desublimator by water spraying at 70° C. Gaseous mixture with solid phthalic anhydride passed through the vessel in the separator. The vessel was contracted to 60 mm and, after the pass through the tube of the same diameter and of the length 400 mm, it entered the lower part of the seaparator. In the connected reception well 1.93 kg of phthalic anhydride per hour was trapped on average. In the filter, having the size of openings of 5 mm, 0.04 kg/h was trapped. In the sum 1.97 kg/h, i.e. 99.5% of phthalic anhydride was separated.

EXAMPLE 3

Vapour-gaseous mixture of 1% of phthalic anhydride in air at 170° C. in volume amount 70 m$^3$/h (20° C.), which corresponds to the velocity of the flow 1.0 m/s (170° C.), was cooled in a desublimator by spraying water at 60° C. After the pass through the contracted vessel of I.D. 72 mm of the length 500 mm, the separated solid phthalic anhydride was continuously melted in a receiver, which was, in its upper part, heated to 125° C. and in its lower part to 150° C. The melt of phthalic anhydride was continuously taken off through siphoning at an average amount of 4.6 kg/h. In the additional filter with the openings of 1 mm no entrainment was observed. On the walls only a thin coat was observed and, in the filter, the needle crystals of phthalic anhydride.

EXAMPLE 4

In the same procedures as in examples 1 & 2 a mixture was cooled under the conditions identical with those in example 2.

The mixture originated at phthalic anhydride production by oxidation of o-xylen and it contained phthalic anhydride, 5% maleinanhydride and 2% of phthalic acid. Desublimed phthalic anhydride contained 0.06% of maleinanhydride, 0.08% of malein acid and 0.1% of phthalic acid.

EXAMPLE 5

One of the possible apparatuses for the process according to the invention is shown in FIG. 1. The apparatus consists of the body of the separator 2 including a housing which is connected to the outlet of the desublimator 1. The desublimator includes means in a wall portion of the desublimator to cool vapor-gaseous mixtures such as jets or nozzles 1b for introduction of water, typically in the form of a water spray. Air is simultaneously introduced to the desublimator through inlet opening 1c located in a wall portion of the desublimator adjacent an inner gas-permeable wall section 1a. A part of separator 2 is a conical vessel 4, receiver well 3 and outlet device 8. To the separator body the filtration equipment 20 can be connected.

In the upper part of the separator 2, there is conical vessel 4, which is connected to outlet 6 of desublimator 1 by its greater cross-section and its smaller cross-section is provided with outlet throat 5 which is a gate of receiver well 3. The diameter of outlet throat 5 of the conical vessel 4 corresponds to ½ to 1/5 of the diameter of outlet throat 6 of desublimator 1. The well 3 has conical and cylindrical zones and into its lower part 7 the outlet device 8 is introduced, e.g. in the form of sucking siphon as it is shown in FIGURE or in the form of worm conveyer or another suitable contruction. The well 3 is equipped with heating elements 18 along the greater part of its length. The filtration equipment 20 is connected to the annular space 11 of separator 2 by tube 25. In the upper part of the equipment there are filters 24 from wire net. In the lower part there is a well 21 similarly constructed as that at separator 2. It is also equipped with heating 26. Filtration equipment 20 has in its upper part outlet throat 23 for gas and in its lower part outlet 22, which is connected with the well 3 of the separator 2.

The apparatus work as follows: Gaseous mixture with solid naphthalene or phthalic anhydride in form of wool flakes leaves the output throat of desublimator with velocity of 0.15 to 1 m/s. Due to the contraction of the cross-section of the conical vessel the flow of the mixture is accelerated. Due to the increased velocity of 0.6 to 25 m/s, the flakes form agglomerates and become more compact. After leaving the outlet throat they easily separate from gaseous mixture and fall into the well 3, where they pile as product 27. The selection of ratio of cross-sections of outlet throat 6 of desublimator 1 and of outlet throat 5 of the conical vessel 4 separator housing 9, depends on the angle of slope of wool agglomerates of phthalic anhydride.

In well 3 the product 27 is gradually melted by heat at 140° to 180° C. The melt of phthalic anhydride is removed from the lower part 7 of the well 3 with outlet device 8 and is passed to further treatment.

The remaining gaseous mixture goes from the upper space of separator 2 into the filtering device 20, where 1 to 5% of the total amount of phthalic anhydride in the mixture is separated on filters made from wire net.

The separated product 28 is melted in the well 21 of the filtering device 20 similarly as it is done in the separator 2 and the resulting melt is introduced into the well of the separator 2.

The temperature of the surface of heating device 18 of the well 3 near the entrance into the well is kept as low as possible to avoid sublimation of phthalic anhydride. In most cases the temperature 140° to 180° C. is sufficient. This substantially simplifies transport of phthalic anhydride from the desublimator 1 and decreases the cost of transport and of equipment as well as substantially decreases the explosion hazard connected with the transport of powdered phthalic anhydride.

What is claimed is:

1. A method for separation of phthalic anhydride from a gaseous stream which originates from desublimation cooling of vapor of phthalic anhydride by water spraying in a desublimator, wherein the mixture upon exiting an outlet from the desublimator contains solid phthalic anhydride in the form of flakes and the velocity of its flow is 0.15 to 1 m/s, wherein the method comprises accelerating the flow of the gaseous stream after desublimation through a frusto-conical member to a velocity of 0.6 to 25 m/s to agglomerate said solid phthalic anhydride and subsequently decelerating said flow to a velocity of 0.15 to 1 m/s for gravitationally separating 95 to 99% of the phthalic anhydride in the form of agglomerated solids from the gaseous stream and recovering the gaseous stream.

2. The method of claim 1 also comprising continously melting the separated solid phthalic anhydride by gradually increasing the temperature from about 120° to 160° C. to about 140° to 180° C.

3. The method of claim 2 also comprising filtering off the desublimated solids which were not separated by the gravitational separation and continuously melting said solids by gradually increasing the temperature from about of 120° to 160° C. to about of 140° to 180° C.

4. An apparatus for separating solid particles from gaseous mixtures, especially for the separation of phthalic anhydride from a mixture originating from the desublimation of phthalic anhydride vapor in a desublimator, comprising a separator including a housing, in the upper part of which, proximate a housing inlet, a conical vessel is positioned defining an annular space between the housing and the conical vessel, the conical vessel having an inlet throat and an outlet throat, the inlet throat having a greater cross-section than the outlet throat, a well connected to the housing for the gravitational accumulation of solids, the well including a heater to melt solids collected in the well and being located in the lower part of the housing and connected to an outlet device, with the annular space being connected to an outlet for the gaseous mixture located in the upper part of the housing.

5. The apparatus of claim 4 wherein the inlet throat of the conical vessel is connected to the outlet of a desublimator and the ratio of cross-sections of the outlet throat of the conical vessel to the inlet throat of the conical vessel is from 0.5 to 0.2 to 1.

6. The apparatus of claim 4 wherein filtration equipment comprised of filters from wire net is connected to the outlet for the gaseous mixture, which forms an inlet to the filtration equipment, the filtration equipment being provided with an outlet for the gaseous mixture and a well having an outlet which is connected with the well of the separator.

* * * * *